United States Patent
Ohashi et al.

(10) Patent No.: US 9,546,987 B2
(45) Date of Patent: Jan. 17, 2017

(54) SYSTEM AND PROGRAM FOR CONTROLLING LIQUID CHROMATOGRAPH

(75) Inventors: Hiroshi Ohashi, Otsu (JP); Tadayuki Yamaguchi, Kawasaki (JP); Hidetoshi Terada, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 210 days.

(21) Appl. No.: 14/233,009

(22) PCT Filed: Jun. 28, 2012

(86) PCT No.: PCT/JP2012/066583
§ 371 (c)(1),
(2), (4) Date: Jan. 29, 2014

(87) PCT Pub. No.: WO2013/011818
PCT Pub. Date: Jan. 24, 2013

(65) Prior Publication Data
US 2014/0157878 A1 Jun. 12, 2014

(30) Foreign Application Priority Data
Jul. 15, 2011 (JP) .................... 2011-157130

(51) Int. Cl.
*G01N 30/34* (2006.01)
*G01N 30/46* (2006.01)

(52) U.S. Cl.
CPC ............ *G01N 30/34* (2013.01); *G01N 30/466* (2013.01)

(58) Field of Classification Search
CPC ...... G01N 30/34; G01N 30/36; G01N 30/466; G06F 3/14; G06F 15/00
(Continued)

(56) References Cited

U.S. PATENT DOCUMENTS 4,239,623 A * 12/1980 Schrenker .............. B01D 15/08
210/198.2

FOREIGN PATENT DOCUMENTS

| JP | 60-253970 | 12/1985 |
|----|-----------|---------|
| JP | 2005-127814 A | 5/2005 |

OTHER PUBLICATIONS

Non-Patent Literature ChromQuest 5.0 Chromatography Data System User Guide, Mar. 2008, Thermo Fisher Scientific.*

(Continued)

*Primary Examiner* — Laura Martin
*Assistant Examiner* — Irving A Campbell
(74) *Attorney, Agent, or Firm* — Sughrue Mion, PLLC

(57) ABSTRACT

A liquid chromatograph control system for controlling an operation of a liquid chromatograph which uses a mobile phase composed of a mixture of solvents and which has the function of performing a gradient analysis while temporally changing the mixture ratio of the solvents. The system initially requests a user to set a basic gradient profile (Step S12), and subsequently, to set the number of steps to change the mixture ratio of the mobile phase at the beginning and/or at the end of the gradient process as well as the amount of change in the mixture ratio per step (Step S13). After that, based on the possible combinations of the mixture ratios of the mobile phase at the beginning and at the end of the gradient process computed from the contents of information entered in the previous steps, a plurality of gradient profiles corresponding to those combinations are created (Step S14).

3 Claims, 4 Drawing Sheets

(58) Field of Classification Search
USPC .................. 73/61.52, 61.56, 23.41, 61.55
See application file for complete search history.

(56) References Cited

OTHER PUBLICATIONS

Non-Patent Literature HPLC-MS, archived on Feb. 3, 2011, accessed at http://web.archive.org/web/20110203012107/http://www.forumsci.co.il/hplc/hplc-operation.html.*
Chinese Office Action issued Jul. 30, 2014 in Chinese Patent Application No. 201280035075.2.

* cited by examiner

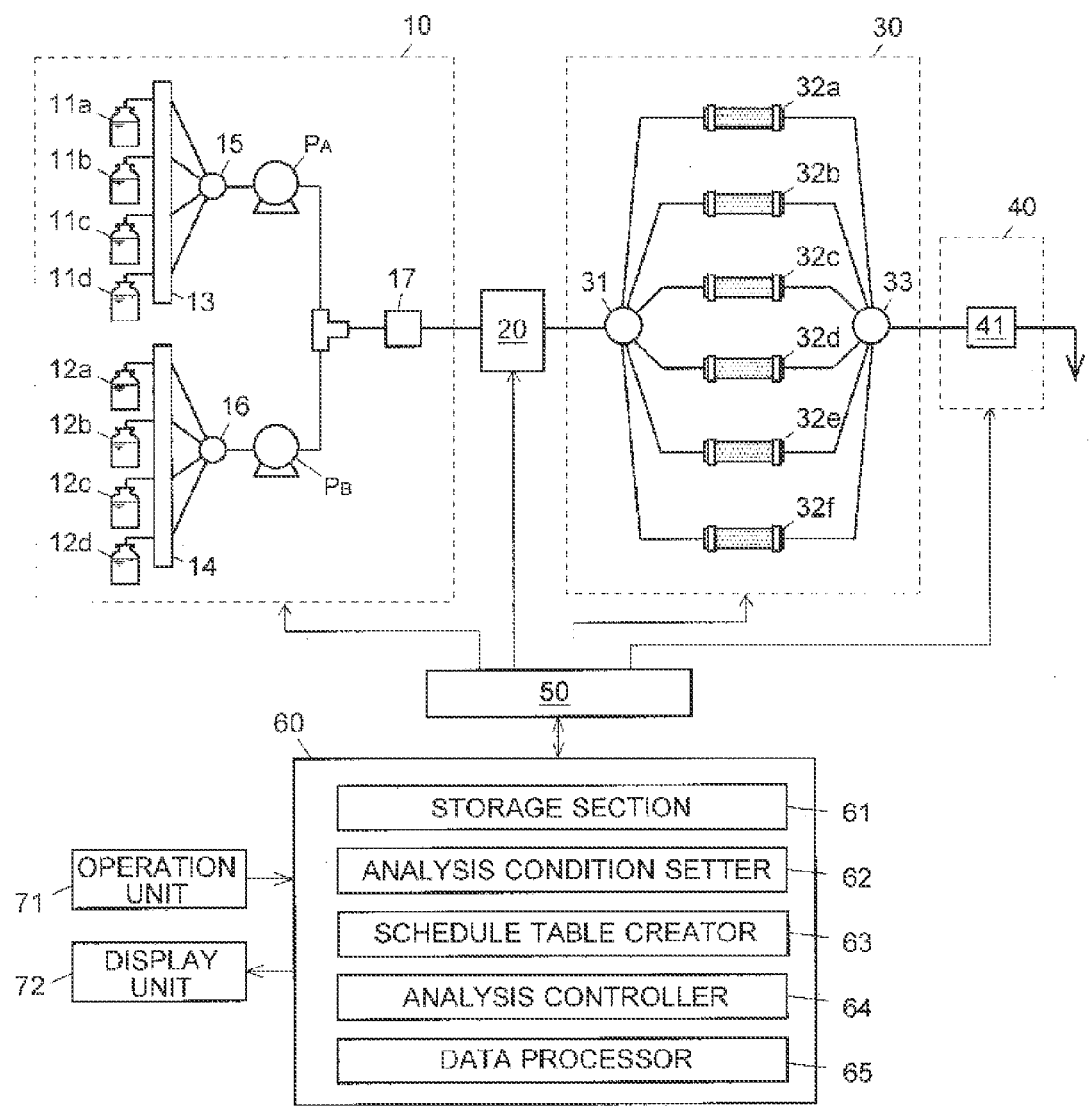

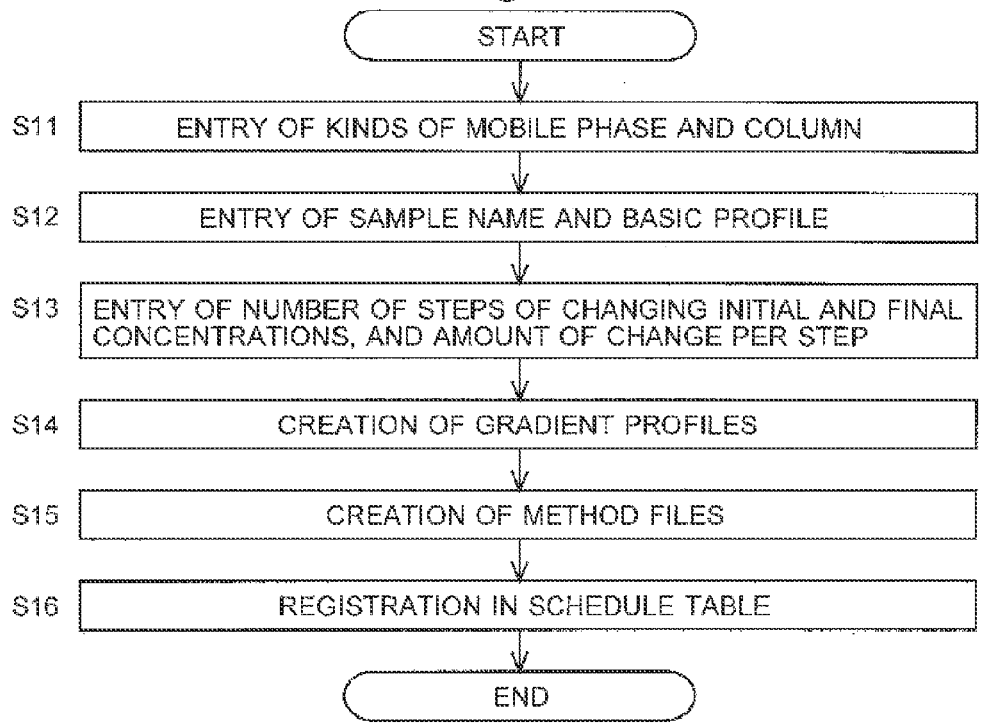
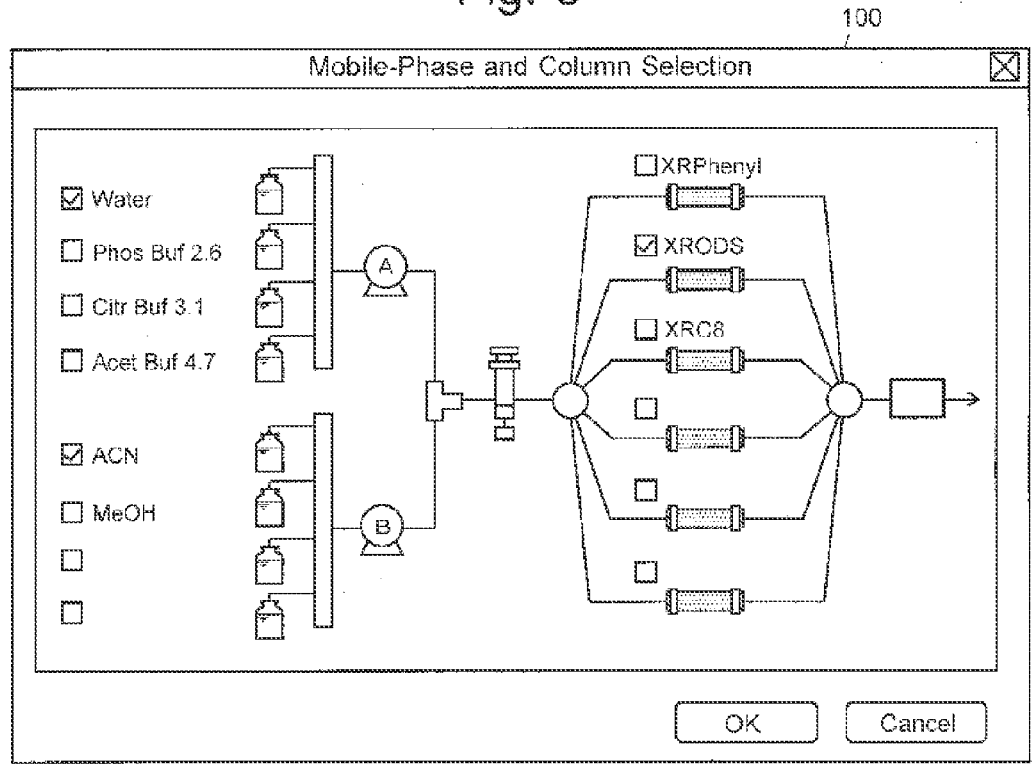

| Analysis No. | Sample Name | Amount of Injection | Method-File Name | Data-File Name | ... |
|---|---|---|---|---|---|
| 1 | — | — | Method 1 | 20110706_XRODS_Water_ACN_5_95 | ... |
| 2 | Sample 1 | 10 | Method 1 | 20110706_XRODS_Water_ACN_5_95 | ... |
| 3 | — | — | Method 2 | 20110706_XRODS_Water_ACN_5_75 | ... |
| 4 | Sample 1 | 10 | Method 2 | 20110706_XRODS_Water_ACN_5_75 | ... |
| 5 | — | — | Method 3 | 20110706_XRODS_Water_ACN_5_55 | ... |
| 6 | Sample 1 | 10 | Method 3 | 20110706_XRODS_Water_ACN_5_55 | ... |
| ⋮ | ⋮ | ⋮ | ⋮ | ⋮ | |

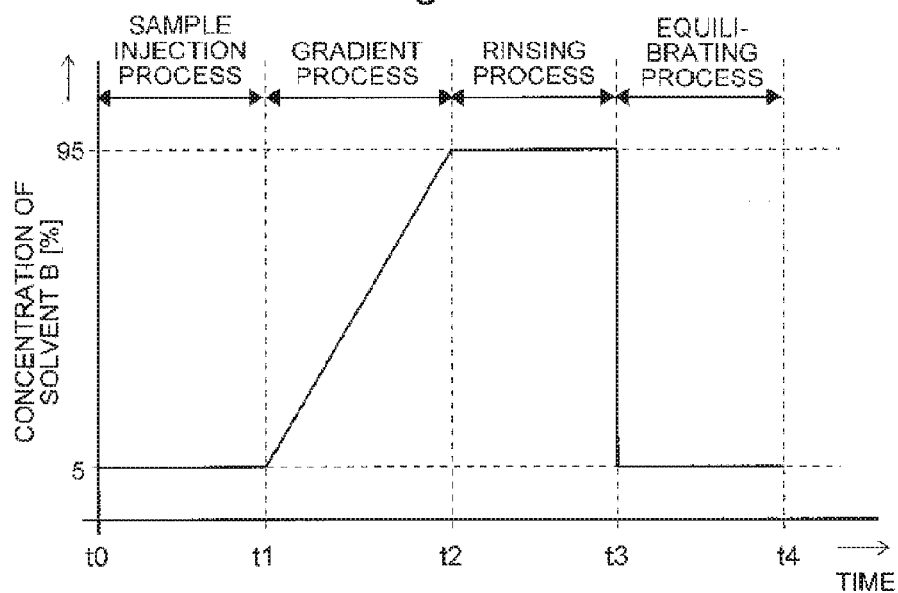

| Analysis No. | Sample Name | Amount of Injection | Method-File Name | Data-File Name | ... |
|---|---|---|---|---|---|
| 1 | Sample 1 | 10 | File 1 | Data 1 | ... |
| 2 | Sample 2 | 10 | File 2 | Data 2 | ... |
| 3 | Sample 3 | 10 | File 3 | Data 3 | ... |
| ⋮ | ⋮ | ⋮ | ⋮ | ⋮ | |

# SYSTEM AND PROGRAM FOR CONTROLLING LIQUID CHROMATOGRAPH

CROSS REFERENCE TO RELATED APPLICATIONS

This application is a National Stage of International Application No. PCT/JP2012/066583 filed Jun. 28, 2012, claiming priority based on Japanese Patent Application No. 2011-157130 filed Jul. 15, 2011, the contents of all of which are incorporated herein by reference in their entirety.

TECHNICAL FIELD

The present invention relates to a system for controlling an operation of a liquid chromatograph and a program to be used in such a control system.

BACKGROUND ART

A liquid chromatograph is composed of a plurality of units, such as an auto-sampler, a pump and a column oven. Operations of those units are controlled according to control signals from a control system.

In recent years, a control system consisting of a personal computer in which a predetermined controlling and processing program is installed is widely used also for such liquid chromatographs in order to generally control analyzing units of the device and to process the thereby collected data. Such a control system has the function of preparing a schedule table in advance of an analysis and automatically performing a continuous analysis of a plurality of samples or similar analyses according to the prepared schedule (for example, see Patent Document 1).

FIG. 7 is one example of the schedule table for a liquid chromatographic analysis. In this table, each row corresponds to one analysis and consists of fields in which necessary information for that analysis is written, such as the sample name, the amount of sample injection, the name of a method file, and the name of a data file in which an analysis result is to be stored. A method file is a file in which operating conditions of the units constituting the liquid chromatograph are specified (those conditions are hereinafter called the "analysis method"). The information written in the file includes various parameters, such as the kinds of mobile phase and column to be used in the analysis as well as the flow rate of the pump and the temperature of the oven during the analysis.

After the schedule table is thus prepared, when the initiation of the analysis is ordered, an analysis of a number of samples is automatically performed, with the samples sequentially selected and the analysis conditions appropriately set according to the schedule.

In such a liquid chromatograph, one sample may be subjected to an analysis under various conditions so as to find an optimal condition for analyzing that sample. Such a technique is called the "method scouting." In the method scouting, the user previously prepares a plurality of different method files with various combinations of the aforementioned parameters, and furthermore, as shown in FIG. 7, assigns a different method file to each row of the schedule table, with the same sample name and the same amount of sample injection specified in all the rows, before ordering the initiation of the analysis. As a result, a series of analyses are sequentially performed under various conditions as described in the method files specified in each row of the table. The chromatogram data obtained as the analysis result are stored, for each analysis, into one data file and saved in a storage device, such as a hard disk drive. The user refers to the chromatogram data stored in the storage device and find the analysis condition under which an optimal analysis result has been obtained. The analysis condition thus found is chosen as the analysis method to be applied in an analysis of the sample in question.

As one of the analytical techniques using a liquid chromatograph, a gradient liquid-sending method is known. In this method, a mixture of two or more solvents having different natures, such as water and an organic solvent, is used as a mobile-phase liquid to be sent into a column, with the mixture ratio of the solvents being varied with time. This technique is particularly useful for clearly separating a multi-component sample into its components.

To perform an analysis of a sample by the gradient liquid-sending method (which is hereinafter called the "gradient analysis"), a user sets a gradient profile (e.g. as shown in FIG. 6) as one of the analytical parameters to be included in the method file. The gradient profile shows the target values of the mobile-phase composition with respect to the lapse time from the beginning of the analysis. The example of FIG. 6 is a profile for a gradient analysis in which a mixture of solvents A and B is used as the mobile phase. The composition of the mobile phase is represented by the percentage of the solvent B in the mixture. A solvent with a low eluting power (e.g. a more polar solvent in the case of a reverse-phase analysis) is used as the solvent A, while a solvent with a high eluting power (e.g. a less polar solvent in the case of a reverse-phase analysis) is used as the solvent B. After a sample is injected at time t0, the percentage of the solvent B is initially maintained at a low level for a predetermined period of time (from t0 to t1), whereby the components in the sample are temporarily adsorbed in the column. After that, the percentage of the solvent B is linearly increased with time (from t1 to t2), whereby the components are sequentially and individually eluted from the column according to their properties (e.g. the polarity). Subsequently, the percentage of the solvent B is maintained at a high level for a certain period of time (from t2 to t3) so as to discharge residual components from the column, after which the mobile phase is restored to its initial composition. This state is further maintained for a certain period of time (from t3 to t4) until the inside of the column is equilibrated.

In the following description, the process corresponding to the period of time from t0 to t1 is called the "sample injection process", the process corresponding to the period of time from t1 to t2 is called the "gradient process", and the process corresponding to the period of time from t2 to t3 is called the "equilibrating process". In some cases, the sample injection process is omitted and the gradient process is initiated simultaneously with the injection of the sample.

BACKGROUND ART DOCUMENT

Patent Document

Patent Document 1: JP-A 2005-127814

SUMMARY OF THE INVENTION

Problem to be Solved by the Invention

Setting such a gradient profile in a conventional liquid chromatograph requires users to manually enter the time values of t1, t2, t3 and t4 as well as the composition of the mobile phase at each of the four points in time t0, t1, t2 and t3. Such a setting task by the user will be cumbersome and complicated in the case of the method scouting in which a plurality of gradient analyses with different gradient profiles are to be performed.

In the method scouting, the number of analyses generally tends to be large since various analyzing conditions need to be explored. Accordingly, a large number of data files are created as analysis results, and users must open each data file to grasp the conditions under which the analysis result recorded in the file was obtained.

The present invention has been developed to solve the previously described problem, and its primary objective is to provide a liquid chromatograph control system which can reduce the time and labor for the manual task of setting gradient profiles in the case of performing gradient analyses using various gradient profiles. The secondary objective is to provide a liquid chromatograph control system which allows users to easily determine the conditions under which the analysis result recorded in each data file was obtained even if a large number of data files have been created.

Means for Solving the Problem

The present invention aimed at solving the previously described problem is a liquid chromatograph control system for controlling an operation of a liquid chromatograph having the function of performing a gradient analysis while temporally changing the mixture ratio of a plurality of solvents composing a mobile phase, including:

a) a mixture ratio entry section for allowing a user to enter the mixture ratio at the starting point of a process of continuously changing the mixture ratio of the solvents as well as the mixture ratio at the ending point of the same process;

b) a change entry section for allowing a user to set the number of times of changing at least one of the mixture ratios at the starting point and the ending point as well as the amount of change per one changing operation;

c) a gradient profile creating section for creating a gradient profile showing target values of the mixture ratio of the solvents at each point in time during one gradient analysis, the gradient profile creating section having the function of making combinations of possible values of the mixture ratio at the starting point and possible values of the mixture ratio at the ending point based on the contents of information entered through the mixture ratio entry section and the change entry section, and the function of creating a plurality of gradient profiles respectively corresponding the aforementioned combinations; and d) a control section for controlling the liquid chromatograph so as to sequentially perform gradient analyses according to the plurality of gradient profiles.

The "process of continuously changing the mixture ratio of the solvents" corresponds to the previously described gradient process.

In a preferable mode of the present invention, the liquid chromatograph control system further includes:

e) an analysis result storage section for storing, in data files, results of a plurality of gradient analyses performed according to the plurality of gradient profiles, with the result of each gradient analysis individually stored in one data file; and f) a data file auto-naming section for naming the data files in such a manner that the file name of a data file containing a result of a gradient analysis includes at least one of the following items of information: the name of a column used in the analysis, the name of a solvent used in the analysis, the mixture ratio at the starting point, and the mixture ratio at the ending point.

Effect of the Invention

The liquid chromatograph control system according to the present invention having the previously described configuration can reduce the time and labor for the setting task to be done by users in the case of continuously performing a plurality of gradient analyses according to various gradient profiles, since the system does not require users to do the task of entering and setting an individual gradient profile for each analysis as in the conventional case.

Providing the system with the previously described data file auto-naming section allows users to easily determine under what conditions the analysis result recorded in each data file was obtained, without opening the file.

BRIEF DESCRIPTION OF THE DRAWINGS

FIG. 1 is a schematic configuration diagram of a liquid chromatograph having a control system according to one embodiment of the present invention.

FIG. 2 is a flowchart showing an operation of the control system according to the embodiment.

FIG. 3 shows a window for selecting the mobile phase and column in the embodiment.

FIG. 4 shows a window for the detailed setting of the gradient analysis in the embodiment.

FIG. 5 shows a schedule table in the present embodiment.

FIG. 6 shows one example of the gradient profile.

FIG. 7 shows a conventional schedule table.

MODE FOR CARRYING OUT THE INVENTION

One embodiment of the liquid chromatograph control system according to the present invention is hereinafter described with reference to the attached drawings. FIG. 1 is a schematic configuration diagram of a liquid chromatograph having the control system according to the present embodiment.

The present liquid chromatograph includes: a liquid-sending unit 10; an auto-sampler 20; a column oven 30; a detection unit 40; a system controller 50 for controlling each of these elements; a control system 60 for managing the analyzing operation via the system controller 50 and for analyzing and processing data obtained with the detection unit 40; an operation unit 71 including a keyboard and a mouse connected to the control system 60; and a display unit 72 including a display device.

In the liquid-sending unit 10, a solvent A drawn by a liquid-sending pump $P_A$ and a solvent B drawn by a liquid-sending pump $P_B$ are mixed with each other by a gradient mixer 17 and sent to a column. Each of the liquid-sending pumps $P_A$ and $P_B$ has four solvent containers connected to it via a solvent selection valve 15 or 16 and via a deaeration unit 13 or 14, respectively. The solvent containers 11$a$-11$d$ connected to the liquid-sending pump $P_A$ contain, for example, water-based solvents (i.e. solvents whose main component is water). By appropriately changing the setting of the solvent selection valve 15, one of the four solvent containers 11$a$-11$d$ can be selected so that the solvent in the selected container is drawn by the liquid-sending pump $P_A$ as the solvent A. On the other hand, the solvent containers 12$a$-12$d$ connected to the liquid-sending pump $P_B$ contain, for example, organic-based solvents (i.e. solvents whose main component is an organic solvent). By appropriately changing the setting of the solvent selection valve 16, one of the four solvent containers 12a-12d can be selected so that the solvent in the selected container is drawn by the liquid-sending pump $P_B$ as the solvent B. Each of the liquid-sending pumps $P_A$ and $P_B$ can be controlled so that its flow rate changes with time, whereby a gradient liquid-sending process in which the mixture ratio of the solvents A and B changes with time can be performed. The column oven 30 contains six columns 32a-32f provided with passage-switching units 31 and 33 for selectively connecting one of the columns to the mobile-phase passage. The detection unit 40 includes a detector 41, such as a photodiode array (PDA) detector.

The control system 60 includes, as its functional blocks, a storage section 61, an analysis condition setter 62, a schedule table creator 63, an analysis controller 64 and a data processor 65. The substance of the control system 60 is a personal computer, with various functions (which will be described later) realized by executing a dedicated controlling and processing software program installed in the computer. The analysis controller 64 corresponds to the control section in the present invention, while the analysis condition setter 62 corresponds to the gradient profile creating section in the present invention. The analysis condition setter 62 and the operation unit 71 cooperate with each other to function as the mixture ratio entry section and the change entry section in the present invention. The data processor 65 corresponds to both the analysis result storage section and the data file auto-naming section in the present invention.

A normal analyzing operation in one gradient analysis using the aforementioned liquid chromatograph is as follows: Under the control of the system controller 50 directed by the analysis controller 64 in the control system 60, each of the solvent selection valves 15 and 16 selects one solvent container, allowing the solvent contained in the selected solvent container to be drawn at a predetermined rate by the corresponding liquid-sending pump $P_A$ or $P_B$. The solvents A and B which are respectively drawn by the liquid-sending pumps $P_A$ and $P_B$ are uniformly mixed with each other in the gradient mixer 17. The obtained mixture serves as the mobile phase and is supplied through the auto-sampler 20 into a column. The auto-sampler 20 is provided with a rack holding one or more sample bottles (vials). Under the control of the system controller 50, the auto-sampler 20 selects a predetermined sample, collects the sample, and injects it into the mobile phase at a predetermined point in time. Being carried by the mobile phase, the injected sample is introduced into one of the columns 32a-32f.

As shown in the gradient profile in FIG. 6, the flow rates of the liquid-sending pumps $P_A$ and $P_B$ are initially controlled so that the solvent B is maintained at a low level and the solvent A at a high level until a predetermined period of time lapses from the injection of the sample (from t0 to t1: the sample introduction process). Since the solvent used as the solvent A has a weak eluting power, the components in the sample are temporarily adsorbed in the column. Subsequently, the flow rates of the liquid-sending pumps $P_A$ and $P_B$ are changed with time so as to increase the percentage of the solvent B (from t1 to t2: the gradient process). Since the solvent used as the solvent B has a strong eluting power, the components adsorbed in the column are individually and sequentially eluted from the column according to their degree of polarity, to be introduced into the detection unit 40.

In the detection unit 40, the components are individually and sequentially detected by the detector 41, which generates detection signals corresponding to the concentration of each component. The signals are converted to digital data and sent to the control system 60 via the system controller 50. In the control system 60, the received data are stored in the storage section 61 provided on a hard disk or similar storage device. The data are also subjected to a predetermined process by the data processor 65 to create a chromatogram and display it on the screen of the display unit 72. Subsequently, the solvent B is supplied at a high concentration for a predetermined period of time to rinse the column (from t2 to t3: the rinsing process), after which the mobile phase is restored to its original composition and supplied for a predetermined period of time to equilibrate the column (from t3 to t4: the equilibrating process).

Figure 4:
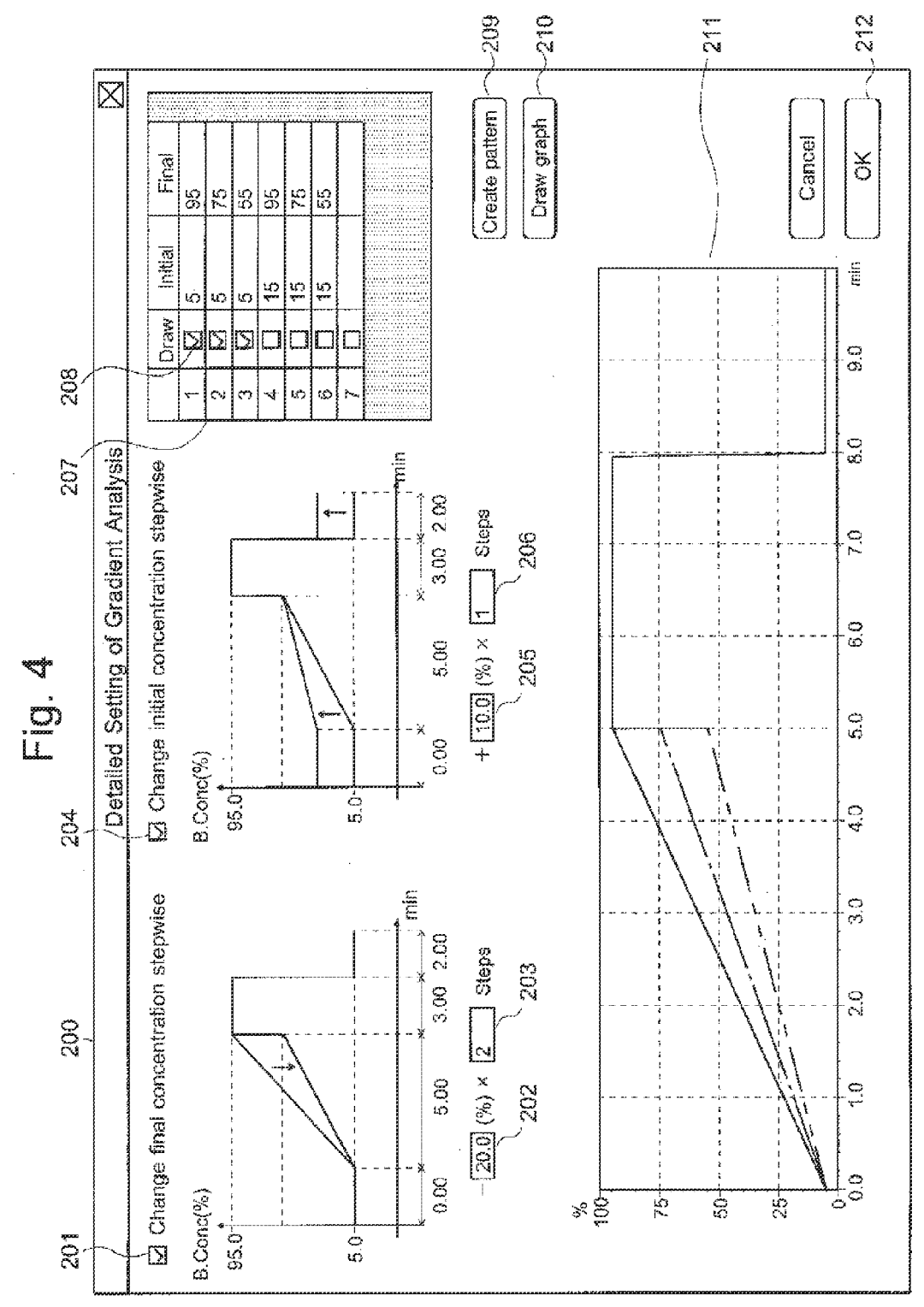

As a characteristic operation of the liquid chromatograph control system of the present embodiment, the operation of preparing method files and a schedule table is hereinafter described with reference to FIGS. 2-5. FIG. 2 is a flowchart showing the process steps of preparing method files and a schedule table. FIGS. 3 and 4 show examples of windows on the screen of the display unit 72. FIG. 5 shows one example of the schedule table in the present embodiment.

Initially, by using the operation unit 71, the user orders the analysis condition setter 62 to perform gradient analyses for a method scouting. In response to this operation, a window 100 for selecting a mobile phase and column (which is hereinafter called the "mobile-phase and column selection window 100"), as shown in FIG. 3, is shown on the screen of the display unit 72. On this window 100, the user selects the kind of solvent to be used as the solvent A, the kind of solvent to be used as the solvent B, and the kind of column (Step S11).

After the setting on the mobile-phase and column selection window 100 is completed, the analysis condition setter 62 displays a basic setting window (not shown) on the screen of the display unit 72. On the basic setting window, the user sets the name of the sample to be analyzed, the amount of injection of the sample, and the basic pattern of the gradient profile (which is hereinafter called the "basic profile") (Step S12). The basic profile is a gradient profile to be used as a basis for a plurality of gradient analyses to be performed in the method scouting. The user can design the basic profile by entering the following items of information on the basic setting window: the execution times of the sample introduction process, the gradient process, the rinsing process and the equilibrating process; the composition of the mobile phase at the beginning of the gradient process; the composition of the mobile phase at the end of the gradient process; and the composition of the mobile phase in the rinsing process. The composition of the mobile phase can be specified by setting the percentage of the solvent B in the mobile-phase liquid after the mixture (i.e. solvent A+solvent B). In the following description, the percentage of the solvent B at the beginning of the gradient process is called the "initial concentration of the solvent B", and the percentage of the solvent B at the end of the gradient process is called the "final concentration of the solvent B." The initial and final concentrations of the solvent B correspond to the mixture ratios at the starting and ending points in the present invention, respectively.

After the setting on the basic setting screen is completed, the analysis condition setter 62 displays a window 200 for the detailed setting of the gradient analysis (which is hereinafter called the "gradient analysis setting window 200"), as shown in FIG. 4, on the screen of the display unit 72. On this window, the user designs gradient profiles to be used in a plurality of gradient analyses to be performed in the method scouting. This task does not require the user to enter and set an individual gradient profile for each gradient analysis; what should be set is: how many times each of the initial and final concentrations of the solvent B should be changed stepwise from the basic profile, and by what amount the concentration of the solvent B should be changed in each step (Step S13).

Specifically, the user initially checks the "Change the final concentration stepwise" box 201 located in the upper left section of the gradient analysis setting window 200. Below this checkbox 201, a graph showing one example of the gradient profile is displayed, on which a downward arrow is superposed to indicate the direction in which the final concentration is to be changed. The execution times of the processes specified in the basic profile on the basic setting window are shown on the horizontal axis of the graph, while the initial and final concentrations of the solvent B as well as the concentration of the solvent B in the rinsing process, which are specified in the basic profile, are shown on the vertical axis of the same graph. Referring to this graph, the user enters numeric values in the two entry fields 202 and 203 provided below the graph to specify how many times the final concentration of the solvent B should be changed and by what amount per step. In the example of FIG. 4, the setting is made so that the concentration will be changed in two steps with a per-step decrement of "20" %.

Subsequently, the user checks the "Change the initial concentration stepwise" box 204 located in the upper middle section of the gradient analysis setting window 200. Below this checkbox 204, a graph showing one example of the gradient profile is displayed, on which upward arrows are superposed to indicate the direction in which the initial concentration is to be changed. The contents of information shown on the vertical and horizontal axes of the graphs are the same as in the previously described graph. Referring to the graph, the user enters numeric values in the two entry fields 205 and 206 provided below the graph to specify how many times the final concentration of the solvent B should be changed and by what amount per step. In the example of FIG. 4, the setting is made so that the concentration will be changed in "one" steps with a per-step increment of "10" %.

Next, when the user clicks the "Create pattern" button 209 located on the gradient analysis setting window 200, a table 207 showing the initial and final concentrations of the solvent B in each of the plurality of gradient analyses is created based on the contents in the checkboxes 201, 204 and the entry fields 202, 203, 205 and 206. In the present example, since the final concentration in the basic profile is 95% and the values in the entry fields 202 and 203 are set so as to change the final concentration in two steps with a per-step decrement of 20%, the possible values of the final concentration are 95%, 75% and 55%. Furthermore, since the initial concentration in the basic profile is 5% and the values in the entry fields 205 and 206 are set so as to change the initial concentration in one step with a per-step increment of 10%, the possible values of the initial concentration are 5% and 15%. Accordingly, there are six (3×2=6) possible combinations of the initial and final concentrations. These six combinations are shown in the table 207, which is displayed on the gradient analysis setting window 200.

When the checkbox 201 is not checked, or when the value in the entry field 202 or 203 is zero, it is determined that the stepwise change of the final concentration is not planned. In this case, a table which shows the combinations of the final concentration in the basic profile and a plurality of initial concentrations calculated from the contents of the entry fields 205 and 206 is displayed on the gradient analysis setting window 200. Similarly, when the checkbox 204 is not checked, or when the value in the entry field 205 or 206 is zero, it is determined that the stepwise change of the initial concentration is not planned. In this case, a table which shows the combinations of the initial concentration in the basic profile and a plurality of final concentrations calculated from the contents of the entry fields 202 and 203 is displayed on the gradient analysis setting window 200. Furthermore, when none of the checkboxes 201 and 204 is checked, or when the value in the entry field 202 or 203 is zero and the value in the entry field 205 or 206 is also zero, it is determined that neither the stepwise change of the initial concentration nor the stepwise change of the final concentration is planned. In this case, a table which shows the only combination of the initial concentration in the basic profile and the final concentration in the same basic profile is displayed on the gradient analysis setting window 200.

Subsequently, when the user clicks the "Draw graph" button 210 on the gradient analysis setting window 200, the analysis condition setter 62 creates a plurality of gradient profiles to be applied in the plurality of gradient analyses to be performed in the method scouting, based on the initial and final concentrations written in each row of the table 207 as well as based on the execution times of the processes specified in the basic profile and the concentration of the solvent B in the rinsing process (Step S14), and then displays a graph 211 showing the created gradient profiles in the lower section of the gradient analysis setting window 200. It should be noted that each row of the table 207 is provided with a checkbox for selecting whether nor not the corresponding profile should be shown on the graph 211. Only the gradient profiles corresponding to the checked rows are shown on the graph 211. In the example of FIG. 4, only the gradient profiles relating to the three combinations written in the three topmost rows are selected from the six combinations listed in the table 207 and shown on the graph 211.

After that, when the user clicks the "OK" button 212 on the gradient analysis setting window 200, the analysis condition setter 62 creates a plurality of method files based on the contents which have been set in the previous steps (Step S15). In each method file, one of the gradient profiles created in Step S14 is written, along with the other parameters, such as the kinds of solvents A, B and the kind of column entered in Step S11. As a result, a plurality of method files which differ from each other only in terms of the gradient profile and are identical in terms of the other parameters are created. Those method files are stored in the storage section 61.

In the previous example, for ease of explanation, it was assumed that the method scouting was performed by variously changing only the gradient profile while allowing only one kind of choice for the solvent A, the solvent B and the column, respectively, on the mobile-phase and column selection window 100. It is also possible to perform the method scouting with two or more kinds of choices provided for the solvent A, the solvent B and the column, respectively. For example, provided that two kinds of solvents A, one kind of solvent B and two kinds of columns have been selected on the mobile-phase and column selection window 100, if the method scouting is performed using the aforementioned six kinds of gradient profiles, the result will be 24 different method files created for the 24 combinations of the choice items (2×1×2×6=24).

After the creation of the method files, a schedule table as shown in FIG. 5 is created by the schedule table creator 63 (Step S16). In this table, each row corresponds to one gradient analysis and includes fields in which necessary information for the analysis is written, such as the sample name, the amount of sample injection, the name of a method file, and the name of a data file. The fields of the sample name and the amount of injection in each row of the schedule table are automatically filled with the values set in Step S12. The field of the method-file name is automatically filled with the name of one of the method files created in Step S15. Furthermore, in the present example, in order to ensure the reproducibility of the analysis, each analysis using one gradient profile is consecutively performed two times, and the data obtained by the second analysis is adopted as the analysis result for the gradient profile concerned (the first and second analyses thus performed are hereinafter called the "void analysis" and the "substantial analysis", respectively). Accordingly, in FIG. 5, two analyses using the same method file are registered in two consecutive rows for each method file, with the first and second rows corresponding to the void and substantive analyses, respectively. The fields of the sample name and the amount of sample injection for the void analysis are left blank, since the void analysis requires no injection of a sample.

As already explained, each row of the schedule table has a field for the name of a data file in which an analysis result is to be stored. In a conventional system, a serial number or similar information is included in the name of the data file. In the system of the present embodiment, a name which shows analysis conditions as shown in FIG. 5 is automatically given to the data file. In the example of FIG. 5, the data-file name includes the following items of information serially connected by underscores: the prefix, the column name, the name of the solvent A, the name of the solvent B, the composition of the solvent B at the beginning of the gradient process, and the composition of the solvent B at the end of the gradient process. The prefix, which is common to all the rows, is an arbitrary character string previously set by users. The portions other than the prefix are filled with appropriate character strings based on the descriptions in the method file specified in the corresponding row.

Subsequently, when the user performs a predetermined operation for initiating the analysis, an automatic analysis according to the schedule table is initiated, in which the gradient analyses using various gradient profiles are sequentially performed.

Chromatogram data obtained as a result of one analysis is stored in one data file for each analysis. Each data file is given the file name written in the corresponding row of the schedule table.

In the example of FIG. 5, the same data-file name is written in both the row of the substantive analysis and that of the corresponding void analysis, which means that the data file created as a result of the void analysis is overwritten with the data file created as a result of the subsequently-performed substantive analysis. This causes no notable problem since users are least likely to refer to the result of the void analysis. However, for example, it is also possible to add to the file name a character string representing the distinction between the void analysis and the substantive analysis so that the result of the void analysis and that of the substantive analysis will be individually stored with different data-file names. Another possible method is to give a name including a serial number or the like to the data file of the void analysis as in the conventional system, so as to allow users to easily distinguish between the data file of the void analysis and that of the substantive analysis. It is also possible to separate the storage location for the data file of the void analysis from the storage location for the data file of the substantive analysis.

As described thus far, with the liquid chromatograph control system according to the present embodiment, even in the case of performing a plurality of gradient analyses with various gradient profiles, it is unnecessary for users to enter and set each individual gradient profile for each of the gradient analyses as in the conventional case. Therefore, the time and labor for the setting task to be done by users in the method scouting is reduced. Furthermore, since each data file in which an analysis result is stored is automatically given a file name which includes a character string representing analysis conditions, users can easily determine under what conditions the analysis result recorded in the data file was obtained, without opening the file.

EXPLANATION OF NUMERALS

10 . . . Liquid-Sending Unit
11a-11d, 12a-12d . . . Solvent Container
$P_A$, $P_B$ . . . Liquid-Sending Pump
15, 16 . . . Solvent Selection Valve
17 . . . Gradient Mixer
20 . . . Auto-Sampler
30 . . . Column Oven
32a-32f . . . Column
40 . . . Detection Unit
41 . . . Detector
50 . . . System Controller
60 . . . Control System
61 . . . Storage Section
62 . . . Analysis Condition Setter
63 . . . Schedule Table Creator
64 . . . Analysis Controller
65 . . . Data Processor
71 . . . Operation Unit
72 . . . Display Unit
200 . . . Gradient Analysis Setting Window

The invention claimed is:

1. A liquid chromatograph comprising:
a liquid-sending unit that changes a mixture ratio of a plurality of solvents composing a mobile phase; and
an analysis condition setting control unit configured to set an analysis condition for a plurality of gradient analyses and to control an operation of the plurality of gradient analyses, where the mixture ratio of the plurality of solvents composing the mobile phase are temporally changed in each of the plurality of gradient analyses and a combination of the mixture ratio at a starting point and the mixture ratio at an ending point of the gradient analysis is different between the plurality of gradient analyses, the analysis condition setting control unit configured to:
a) provide entry locations on a display screen for allowing a user to enter the mixture ratio at the starting point and the mixture ratio at the ending point and allowing a user to set a number of times of changing at least one of the mixture ratios at the starting point and the ending point as well as an amount of change per one operation of changing the mixture ratio at the starting point or the ending point;
b) determine target values by making combinations of possible values of the mixture ratio at the starting point and possible values of the mixture ratio at the ending point based on contents of information entered by the user, and
c) create a plurality of gradient profiles respectively corresponding the aforementioned combinations on the display screen; and d) control the liquid-sending unit so as to sequentially perform the plurality of gradient analyses according to the plurality of gradient profiles.

2. The liquid chromatograph according to claim 1, wherein the analysis condition control unit is further configured to:

e) store a result of each of the plurality of gradient analysis performed according to the plurality of gradient profiles in an individual data file; and f) name the data file in such a manner that a file name of the data file containing a result of a gradient analysis includes at least one of following items of information: a name of a column used in the gradient analysis, a name of a solvent used in the gradient analysis, the mixture ratio at the starting point, and the mixture ratio at the ending point.

3. A non-transitory computer readable medium recording a program for setting an analysis condition for a plurality of gradient analyses and for controlling the operation of a liquid chromatograph having a liquid-sending unit that temporally changes a mixture ratio of a plurality of solvents composing a mobile phase, where the mixture ratio of the plurality of solvents composing the mobile phase are temporally changed in each of the plurality of gradient analyses and a combination of the mixture ratio at a starting point and the mixture ratio at an ending point of the gradient analysis is different between the plurality of gradient analyses, by the following method:

a) providing entry locations on a display for allowing a user to enter the mixture ratio at the starting point and the mixture ratio at the ending point of the same process;

b) allowing a user to set a number of times of changing at least one of the mixture ratios at the starting point and the ending point as well as an amount of change per one operation of changing the mixture ratio at the starting point or the ending point;

c) a gradient profile creating step including determining target values by making combinations of possible values of the mixture ratio at the starting point and possible values of the mixture ratio at the ending point based on the contents of information entered through the mixture ratio entry step and the change entry step, and creating a plurality of gradient profiles respectively corresponding to the aforementioned combinations on the display; and d) a control step for controlling the liquid-sending unit so as to sequentially perform gradient analyses according to the plurality of gradient profiles.

* * * * *